United States Patent [19]

Zalipsky et al.

[11] Patent Number: 5,631,018
[45] Date of Patent: *May 20, 1997

[54] LIPID-POLYMER CONJUGATES AND LIPOSOMES

[75] Inventors: Samuel Zalipsky, Fremont; Martin C. Woodle, Menlo Park; Danilo D. Lasic, Newark; Francis J. Martin, San Francisco, all of Calif.

[73] Assignee: Sequus Pharmaceuticals, Inc., Menlo Park, Calif.

[*] Notice: The term of this patent shall not extend beyond the expiration date of Pat. No. 5,395,619.

[21] Appl. No.: 317,723

[22] Filed: Oct. 4, 1994

Related U.S. Application Data

[63] Continuation of Ser. No. 25,602, Mar. 3, 1993, Pat. No. 5,395,619.
[51] Int. Cl.$^6$ .................................................. A61K 9/127
[52] U.S. Cl. .......................... 424/450; 264/4.3; 264/4.33; 428/402.2
[58] Field of Search .................. 424/450; 428/402.2; 436/829; 525/340, 383, 410, 413, 419, 420; 264/4.1, 4.3, 4.33

[56] References Cited

U.S. PATENT DOCUMENTS 5,013,556  5/1991  Woodle, et al. .......................... 424/450

FOREIGN PATENT DOCUMENTS 7922432  6/1979  United Kingdom.
9002184  1/1990  United Kingdom.

OTHER PUBLICATIONS

Weiner in 'Advanced Drug Delivery Reviews', vol. 3, pp.307–341, Published by 'Elsevier Science Publishers' 1989.

Decher et al. Angew. Makromol. Chem. 166–167, p.71, 1989 (Abstract only).

Primary Examiner—Gollamudi S. Kishore
Attorney, Agent, or Firm—Peter J. Dehlinger; Judy M. Mohr

[57] ABSTRACT

A lipid-polymer conjugate for use in forming long-circulating liposomes is disclosed. The conjugate includes a vesicle-forming lipid having covalently attached to its polar head group, one of the polymers: polyvinylpyrrolidone, polyvinylmethylether, polyhydroxypropyl methacrylate, polyhydroxypropylmethacrylamide, polyhydroxyethyl acrylate, polymethacrylamide, polydimethylacrylamide, polymethyloxazoline, polyethyloxazoline, polyhydroxyethyloxazoline, polyhydroxypropyloxazoline, or polyaspartamide. A method for preparing liposomes containing the lipid-polymer conjugate is also disclosed.

12 Claims, 5 Drawing Sheets

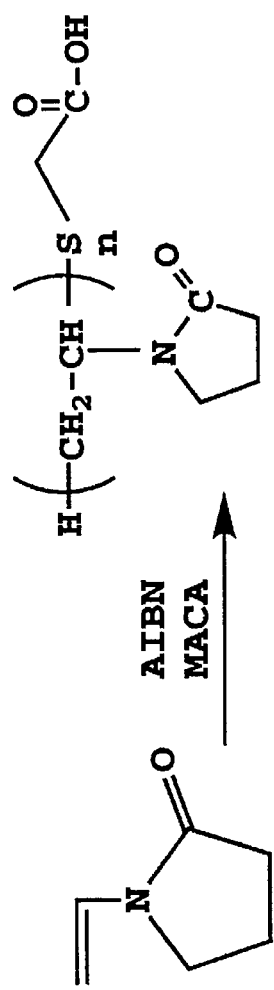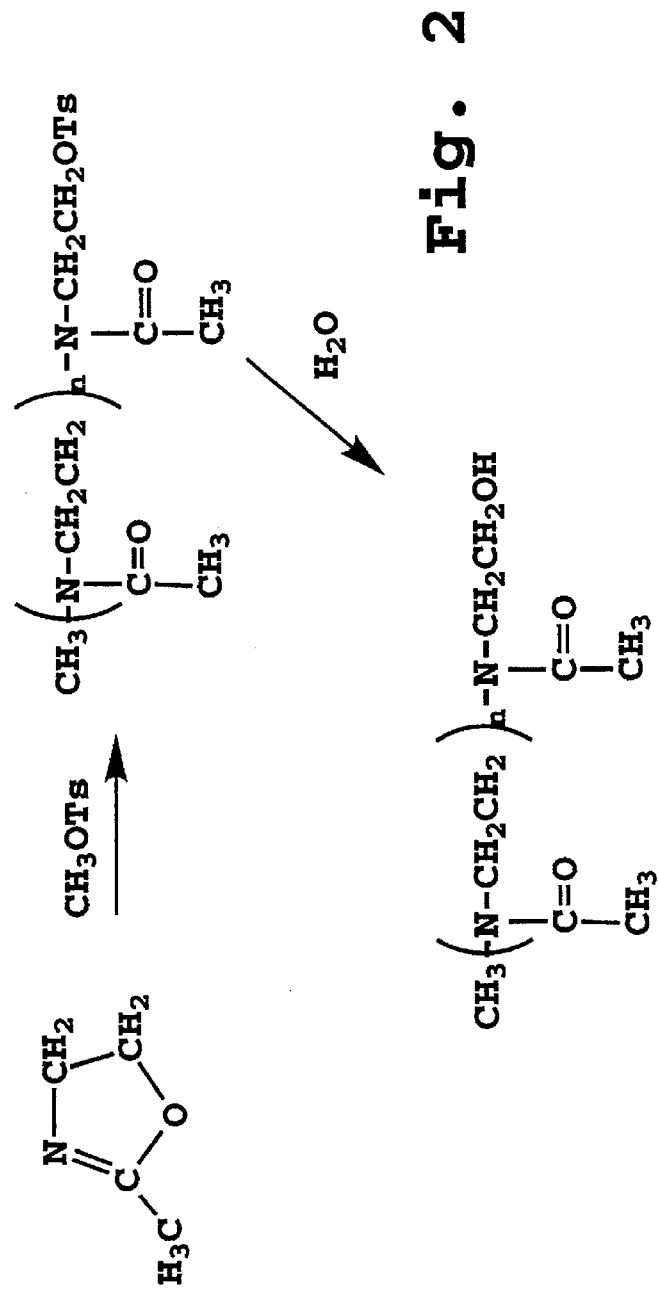
Fig. 1
Fig. 2

LIPID-POLYMER CONJUGATES AND LIPOSOMES

This is a continuation of application Ser. No. 08/025,602 filed Mar. 3, 1993, now U.S. Pat. No. 539,619.

FIELD OF THE INVENTION

The present invention relates to a lipid-polymer conjugate, and to the use thereof in liposomes.

References

Andreani, F., et al., (1986) *J. Bioactive and Comp. Polym.* 1:72–78.

Arnold, K., et al., (1990) *Biochim. Biophys. Acta* 1022:303–310.

Barabas, E.S. (1985) In: Encyclopedia of Polymer Science and Engineering, John Wiley & Sons, pp. 198–257.

Fuchs, O. (1982) In: Polymer Handbook (Brandrup, J., and Immergut, E. H., eds.) John Wiley & Sons, pp. 379–407.

Kawaguchi, et al., (1992) *Carbohydrate Polymers* 18:139–142

McCormick, C., et al., (1987) *Polymer* 28:2317–2323.

McDaniel, R. V., et al., (1986) *Biophys. J.* 49:741–752.

McLaughlin, S. and Whitaker, M. (1988) *J. Physiol.* 396:189–204.

Molyneux, P. (1984) In: Water soluble Synthetic Polymers: Properties and Behavior, Vol.1, CRC Press, pp. 154–163.

Needham, D.C., et al., (1992) *Biochim. Biophys. Acta* 1108:40–48.

Neri, P., et al., (1973) *J. Medicinal Chem.* 16(8):893–897.

Pillai, V.N.R., and Mutter, M. (1981) *Naturwissenschaften* 68:558–566.

Poznansky, M. J., and Juliano, R. L. (1984) *Pharmacol. Rev.* 36:277–336.

Saba, T. M. (1970) *Arch. Intern. Med.* 126:1031–1052.

Saegusa, T., et al. (1972) *Polym. J.* 3:176–180.

Saegusa, T., et al. (1972) *Macromol.* 5:354–358.

Stegmann, T. S., et al. (1989) *Biochem.* 28:1698–1704.

Szoka, F., JR., et al., (1980) *Ann. Rev. Biophys. Bioeng.* 9:467.

Vegotski, A., et al., (1958) *J. Amer. Chem. Soc.* 80:3361.

Veronese, F. M., et al. (1990) *J. Bioactive and Comp. Polym.* 5:167–178.

Woodle, M. C., et al. (1992) *Biophys. J.* 61:902–910.

Woodle, M. C., et al. unpublished.

Zalipsky, S., et al., (1986) *Polymer Preprints* 27(1):1.

Zalipsky, S., et al., (1992) In: Poly (Ethylene Glycol) Chemistry: Biotechnical and Biomedical Applications (J. M. Harris, ed.) Plenum Press, pg. 347–370.

BACKGROUND OF THE INVENTION

Liposomes have the potential as versatile drug carriers in the bloodstream. Because they contain both an inner aqueous compartment and an outer lipophilic shell, liposomes can be loaded with both water-soluble or lipid-soluble drugs. Since liposomes can be formed of natural biochemical lipid, such as phospholipids and cholesterol, they can be broken down by the body without toxic side effects (Poznansky).

Until recently, the potential of liposomes as drug carriers has been limited by the rapid clearance of liposomes from the bloodstream. For example, conventional liposomes may be largely cleared from the bloodstream within 1–2 hours after intravenous administration (Saba).

A variety of approaches for extending the circulation time of liposomes have been proposed. Two of these have been successful in extending the halflife of liposomes in the bloodstream by periods of up to 40–50 hours. In one approach, described in co-owned U.S. Pat. No. 4,837,028, liposomes are formulated with the ganglioside $G_{M1}$ and predominantly rigid lipids. In another general approach, disclosed in co-owned U.S. Pat. No. 5,013,556, liposomes are coated with a layer of polyethylene glycol (PEG) chains.

SUMMARY OF THE INVENTION

It is one general object of the present invention to provide novel lipid-polymer conjugates for use in preparing liposomes having long circulation times in the bloodstream.

It is another object of the invention to provide such long-circulating liposomes.

The invention includes, in one aspect, a lipid-polymer conjugate capable of incorporation into liposomes. The conjugate includes (i) a vesicle-forming lipid having a polar head group, and (ii) covalently attached to the head group, a polymer chain containing a polyvinylpyrrolidone, polyvinylmethylether, polyhydroxypropyl methacrylate, polyhydroxylpropylmethacrylamide, polyhydroxyethyl acrylate, polymethacrylamide, polydimethylacrylamide, polymethyloxazoline, polyethyloxazoline, polyhydroxyethyloxazoline, polyhydroxypropyloxazoline, or polyaspartamide polymer or polymer region. The polymer chain is characterized, in free form, by a solubility in water of at least 5% (w/v) at room temperature, and a solubility in chloroform, acetonitrile, dimethylformamide, and/or methylene chloride of at least about 0.5% (w/v) at room temperature.

In one preferred embodiment, the polymer chain is a homopolymer of one of the specified polymers, more preferably a homopolymer of polyvinylpyrrolidone, polymethyloxazoline, polyethyloxazoline, or polyhydroxypropylmethacrylamide.

In another embodiment, the polymer is a block copolymer of one of the specified polymers and polyethyleneglycol (PEG).

In a further embodiment, the polymer is a random copolymer formed from vinylpyrrolidone and another monomer, such as vinyl acetate or acrylamide.

The above-listed lipid-polymer conjugates can be end-functionalized to permit attachment of therapeutically active compounds to the conjugate.

In another aspect, the invention includes a method for preparing a liposome characterized by an extended blood circulation time. The method includes adding to vesicle-forming lipids, between 1–30 mole percent of the lipid-polymer conjugate and a pharmaceutical compound to form liposomes containing vesicle-forming lipids, the lipid-polymer conjugate, and the pharmaceutical compound in entrapped form, and sizing the liposomes to a selected size in the size range between about 0.05 to 0.2 microns.

Liposomes prepared in accordance with the present invention have characteristic surface properties. For example, liposome surface charge is shielded. Shielding of charge is measured by a reduction in the electrophoretic mobility of the liposomes. Reduced mobility reflects a reduction in the zeta potential of the liposomes.

The electrophoretic mobility of liposomes containing the lipid-polymer conjugate is compared to that of the same liposomes where phosphatidylglycerol is substituted for the lipid-polymer conjugate. Both lipid-polymer conjugate and phosphatidylglycerol contribute a negative charge to the liposome surface, so both liposome preparations have the same net surface charge. However, the electrophoretic mobility of liposomes containing the lipid-polymer conjugate is reduced with respect to liposomes containing phosphatidylglycerol.

These and other objects and features of the present invention will become more fully apparent when the following detailed description of the invention is read in conjunction with the accompanying drawings.

BRIEF DESCRIPTION OF THE DRAWINGS

FIG. 1 illustrates a synthetic reaction scheme for polymerizing vinylpyrrolidone;

FIG. 2 illustrates a synthetic reaction scheme for polymerizing 2-methyloxazoline;

DETAILED DESCRIPTION OF THE INVENTION

I. Definitions

Figure 3:
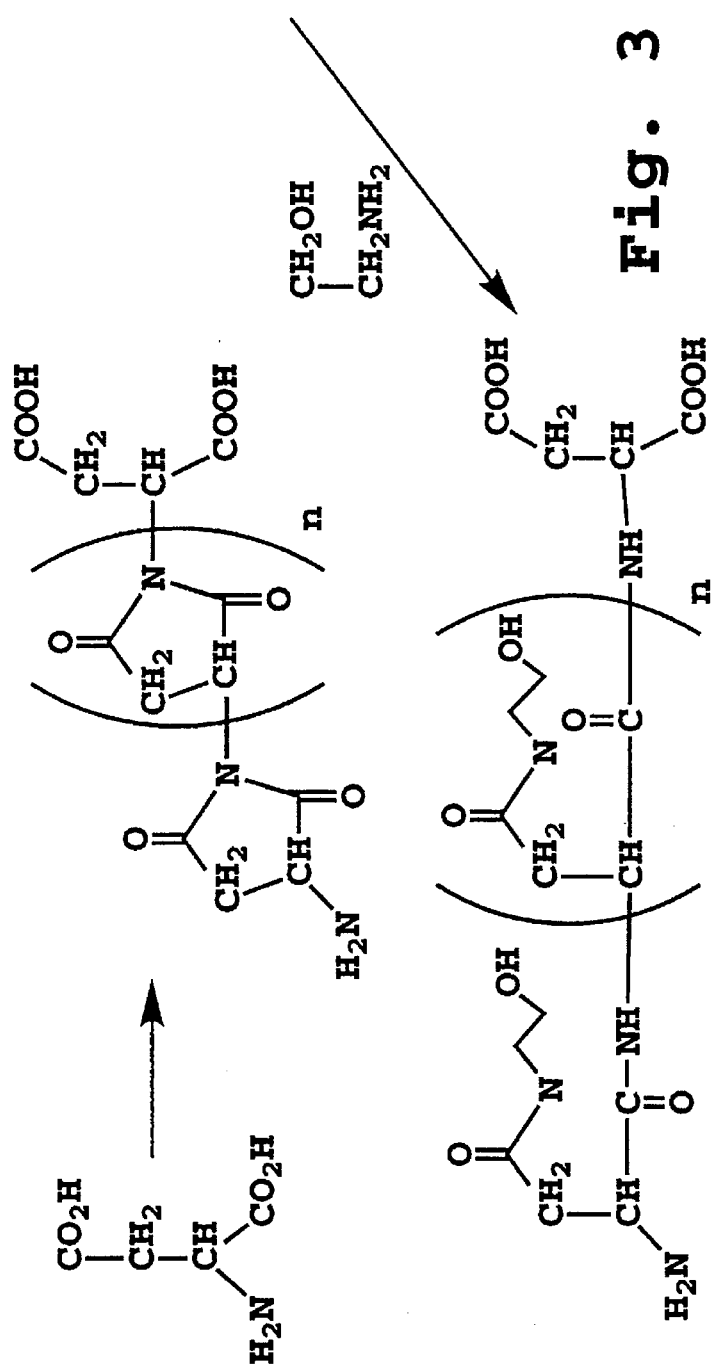
FIG. 3 illustrates a reaction scheme for polyaspartamide synthesis.

Unless indicated otherwise, the terms below have the following definitions:

"Homopolymers" are polymers which have one monomer in their composition.

"Copolymers" are polymers which have more than one type of monomer in their composition. Copolymers may be block copolymers or random copolymers. Block copolymers contain alternating blocks (segments) of different homopolymers. Random copolymers contain random sequences of two or more monomers.

The term "vesicle-forming lipid" is intended to include any amphipathic lipid having a hydrophobic moiety and a polar head group, and which (a) by itself can form spontaneously into bilayer vesicles in water, as exemplified by phospholipids, or (b) is stably incorporated into lipid bilayers in combination with other amphipathic lipids, with its hydrophobic moiety in contact with the interior, hydrophobic region of the bilayer membrane, and its polar head group moiety oriented toward the exterior, polar surface of the membrane.

A polymer is "soluble" in water if the polymer (either a homopolymer or copolymer) is soluble to at least 5% by weight at room temperature at a polymer size between about 20–150 subunits.

A polymer is "soluble" in a polar organic solvent, which may be chloroform, acetonitrile, dimethylformamide, and/or methylene chloride, if the polymer (either a homopolymer or copolymer) is soluble to at least 0.5% by weight at room temperature, at a polymer size between about 20–150 subunits.

II. Preparation of Polymer-Lipid Conjugate

The lipid-polymer conjugate of the invention includes (i) a vesicle-forming lipid having a polar head group, and (ii) covalently attached to the head group, a polymer chain having selected solubility properties, as described below. This section describes the preparation of the conjugate.

A. Vesicle-Forming Lipid

The vesicle-forming lipids used in the lipid-polymer conjugate for forming liposomes of the invention may be selected from a variety of synthetic vesicle-forming lipids or naturally-occurring vesicle-forming lipids. Typically, these lipids may include phospholipids, sphingolipids and sterols.

An important feature of the vesicle-forming lipid used in the lipid-polymer conjugate is that the lipid contain a chemical group at its polar head group suitable for covalent attachment of a polymer chain. The polar head group may contain, for example, an amine group, hydroxyl group, aldehyde group or a carboxylic acid group.

Additionally, the vesicle-forming lipid of the lipid-polymer conjugate is selected to achieve a specified degree of fluidity or rigidity, to control the stability of liposomes in serum and to control the rate of release of entrapped drug from liposomes in the blood stream. These lipids may also be selected, in lipid hydrogenation characteristics, to achieve desired liposome preparation properties. It is generally the case, for example, that more fluidic lipids are easier to formulate and size by extrusion than more rigid lipid components.

A preferred embodiment of the vesicle-forming lipid of the lipid-polymer conjugate is a lipid having two hydrocarbon chains, typically acyl chains, and a polar head group containing a chemical group. Included in this class are the phospholipids, such as phosphatidylcholine (PC), phosphatidylethanolamine (PE), phosphatidylglycerol (PG), phosphatidic acid (PA), phosphatidylinositol (PI), and sphingomyelin (SM), where the two hydrocarbon chains are typically between about 14–22 carbon atoms in length, and have varying degrees of unsaturation.

Phosphatidylethanolamine (PE) is an example of a phospholipid which is preferred for the invention since it contains a reactive amino group which is convenient for lipid coupling to polymers. One preferred PE illustrated in the examples is distearyl PE (DSPE).

B. Polymers

The polymer chain in the conjugate is formed from polyvinylpyrrolidone, polyvinylmethylether, polyhydroxypropyl methacrylate, polyhydroxyethyl acrylate, polymethacrylamide, polydimethylacrylamide, polymethyloxazoline, polyethyloxazoline, or polyaspartamide polymers. The polymer chain preferably contains between 20 to 150 monomer subunits, more preferably 40 to 100 monomer subunits.

The chain may be a homopolymer of the selected polymer or a random or block copolymer containing one or more blocks of the selected polymer spaced by blocks or single subunits of a second polymer. The second polymer may be another of the above-specified polymers or another polymer type, with the limitation that the random or block copolymer meet the following solubility constraints which are important to the properties of the lipid-polymer conjugate in liposomes, as discussed below.

Specifically, the copolymer composition is such that the polymer is characterized, in free form (unattached to the lipid moiety), by a solubility in water of at least 5% (w/v) at room temperature, and a solubility in chloroform, acetonitrile, dimethylformamide, and/or methylene chloride of at least about 0.5% (w/v) at room temperature.

Preferred homopolymers and copolymers, and their methods of synthesis will now be considered.

1. Homopolymer Solubility Properties.

A preferred homopolymer in the invention is polyvinylpyrrolidone (PVP). This polymer is readily soluble (at least 5% by weight) in cold water, as indicated in Table 1 below (Molyneux). The polymer is also soluble (at least 0.5% by weight) in one or more of the polar solvents chloroform, acetonitrile, dimethylformamide, and/or methylene chloride. The PVP polymers shown in Table 1 have subunit numbers ranging from about 60 (PVP7000) to 3500 (PVP400,000). As defined herein, the specified solubilities in water and a polar organic solvent are determined for a polymer having the desired polymer size of between about 20–150 subunits. Therefore, the solubilities listed in Table 1 for polymers of larger sizes, such as a PVP chain with 3,500 subunits, likely reflect minimum solubility values for polymers of smaller sizes, such as PVP chains with about 20–150 subunits.

TABLE 1

| | | |
|---|---|---|
| PVP10000 | water | 10 wt % |
| PVP40000 | chloroform | 3 wt % |
| PVP7000 | methanol | 2 wt % |
| PVP400000 | dimethylformamide | 1 wt % |
| PVP20000 | cyclohexanone | 0.5 wt % |

Considering the solubility properties of other homopolymers mentioned above, poly(dimethylacrylamide) is soluble in water and organic solvents, such as methanol, ethanol, and dioxane. Polymethacrylamide is soluble in water, methanol, ethylene glycol, and acetone, while it is insoluble in hydrocarbons and diethyl ether (Molyneux).

Polyethyl-and polymethyloxazolines are soluble in water, and soluble in acetonitrile, chloroform, and dimethylformamide (Molyneux).

Polyvinylmethylether is soluble in water, and also in alcohols, amines, esters, aromatic hydrocarbons, and chlorinated hydrocarbons (Molyneux).

Polyaspartamide is a polymer derived from aspartic acid and rendered soluble in water by reaction with ethanolamine which generates hydroxyl groups along the polymer chain. This polymer is soluble in water and dimethylformamide (Neri).

Polyhydroxypropyl methacrylate and polyhydroxyethyl acrylate are also soluble in water and one or more of the specified polar organic solvents.

Additionally, the homopolymer can be a derivatized cellulose, such as carboxymethylcellulose, hydroxypropylcellulose, or hydroxyethylcellulose. In underivatized cellulose intermolecular hydrogen-bonding results in decreased solubility of cellulose in water. Derivatizing cellulose hydroxyl groups decreases hydrogen-bonding, and as a consequence increases cellulose solubility in water. Derivatives of cellulose usually are formed with varying degrees of substitution at the hydroxyl groups of C-2, C-3, and C-6.

Preferred derivatized celluloses exhibit the following solubilities. For example, hydroxypropylcellulose and hydroxyethylcellulose are soluble in water, chloroform, acetone, pyridine, cyclohexanone and are not soluble in ethanol, diethyl ether and aliphatic hydrocarbons. Cellulose acetate is soluble in water, methylene chloride, chloroform, tetrahydrofuran, among others. It is insoluble in aliphatic hydrocarbons, ethanol, and benzene (Fuchs).

Alternatively, the polymers in the invention may be copolymers which incorporate the above-named monomers, either as block or random copolymers. For examples, a polymer containing a high percentage of vinylpyrrolidone and another subunit, such as vinylmethylether, methyl acrylate, hydroxypropyl methacrylate, hydroxyethyl acrylate, methacrylamide, and dimethylacrylamide, may be prepared by radical polymerization methods used in PVP synthesis.

Preferred block copolymers with the requisite solubility characteristics are formed to contain one or more alternating blocks of PEG and one of the homopolymers disclosed above. In a preferred embodiment the heteropolymer is a block copolymer consisting of alternating PVP and PEG blocks, or a single blocks of each.

2. Homopolymer Synthesis.

Polyvinylpyrrolidone (PVP), an example of an N-vinyl amide polymer, will be discussed in detail as a preferred embodiment of this aspect of the invention. PVP can be synthesized by free radical, anionic, or cationic polymerization of vinyl pyrrolidone (VP) monomers. Preferably, the monomer is polymerized by the free radical route in the presence of a free radical initiator, such as hydrogen peroxide or azobisisobutyronitrile (AIBN).

As described in Example 1 and illustrated in FIG. 1, VP monomers are incubated with mercaptoacetic acid (MACA) and AIBN to favor synthesis of PVP with a molecular weight of about 6,000. MACA is used in the polymerization reaction to generate a chemical group, a carboxyl group, at a polymer free end for coupling to a vesicle-forming lipid. Additionally, MACA concentrations are varied to synthesize polymers of a desired length. For example, a 0.2 molar MACA concentration is used to synthesize PVP polymers of a molecular weight of about 6,000 daltons. MACA also decreases product heterogeneity, and product may not need further purification by size fractionation (Andreani, Veronese). Alternatively, other mercaptans, such as mercaptoethanol (ME) or mercaptopropanoic acid (MPA), can replace MACA in the polymerization reaction to generate an appropriate terminal group.

A similar free-radical polymerization method is suitable for the synthesis of polyvinylmethylether, polyhydroxypropyl methacrylate, polyhydroxyethyl acrylate, polydimethyl acrylamide, or polymethacrylamide for generating polymers suitable for this invention.

FIG. 2 illustrates a synthetic reaction scheme for a polymerization of 2-methyl-oxazoline (MOZ). In this reaction, MOZ polymerization occurs by a cationic polymerization mechanism. MOZ polymerization is initiated by methyl tosylate which catalyzes a ring opening reaction of 2-methyl-oxazoline. The polymerization reaction is propagated by the polymer "live end" which can cause further 2-methyl-oxazoline ring-opening reactions. After the polymerization reaction an aqueous workup generates a hydroxyl group by displacement of the tosylate group at a polymer end (Saegusa). This hydroxyl group is used for polymer attachment to a vesicle-forming lipid. Reaction conditions are discussed in Example 2.

Nucleophilic reagents, other than water, can be used to provide other functional groups at a polymer end. For example, use of a diamine would generate an amine group at the free end. A similar procedure is used for the synthesis of poly(2-ethyl-oxazoline).

FIG. 3 illustrates a synthetic reaction scheme for the formation of polyaspartamide. Aspartic acid is polymerized by heating for 2–4 hours at 200° C. to generate polysuccinimide with an average molecular weight of 11,000 (Vegotski). Polysuccinimide is reacted with ethanolamine. This results in ring-opening of succinimide groups of the polymer chain to generate poly(hydroxyethyl-(D,L-aspartamide). The terminal carboxylic acid groups are coupled to a vesicle-forming lipid after activation of either or both carboxylic acid groups at one polymer end.

Other homopolymer candidates can be synthesized as follows. To generate cellulose derivatives, cellulose is reacted with chloroacetic acid to form carboxymethylcellulose or with ethylene oxide to form hydroxyethylcellulose. To maximize solubility of derivatized celluloses in water, it is usually necessary to partially hydrolyze the fully derivatized cellulose (Kawaguchi, McCormick). In this manner polymers containing between 40 and 100 sugar units can be generated. This is the desired length for purposes of the invention.

3. Random Copolymer Synthesis.

Figure 4:
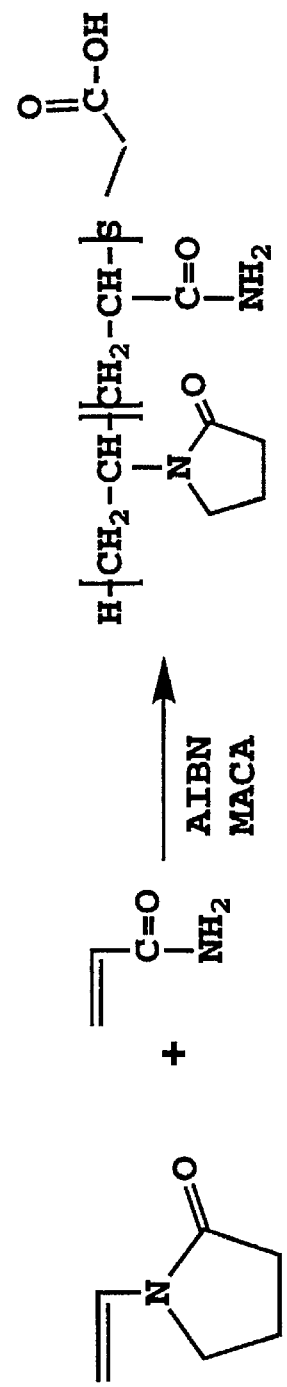
FIG. 4 illustrates a synthetic reaction scheme for random copolymerization of vinylpyrrolidone and methyl acrylate monomers.

FIG. 4 shows the formation of a random copolymer of VP and acrylamide (AA) monomers. As described for the polymerization of VP monomers copolymerization reactions are performed in the presence of a free radical initiator and a terminator such as MACA to introduce an end functional group and to decrease product heterogeneity. The ratio of individual monomers in a polymerization reaction mixture is dependent on the reactivity of each monomer to free radical polymerization and to the monomer ratio desired in the polymerization product (Barabas).

VP copolymerizes readily with a wide variety of other monomers, such as ethyl acrylate, methyl acrylate, methyl methacrylate, maleic anhydride, dimethylaminoethyl methacrylate, acrylamide, methacrylamide, ethylene, vinyl propionate, vinyl caprolactam, and methyl vinyl ketone. The monomers copolymerized with VP preferably possess similar solubility characteristics as does VP, such as methacrylamide monomer.

Alternatively, the monomers copolymerized with VP may possess different solubility characteristics, such as methylmethacrylate monomers. The methylmethacrylate monomer content of the random copolymer is selected so that the polymer product has solubility characteristics similar to those of PVP.

4. Block Copolymer Synthesis.

Figure 5:
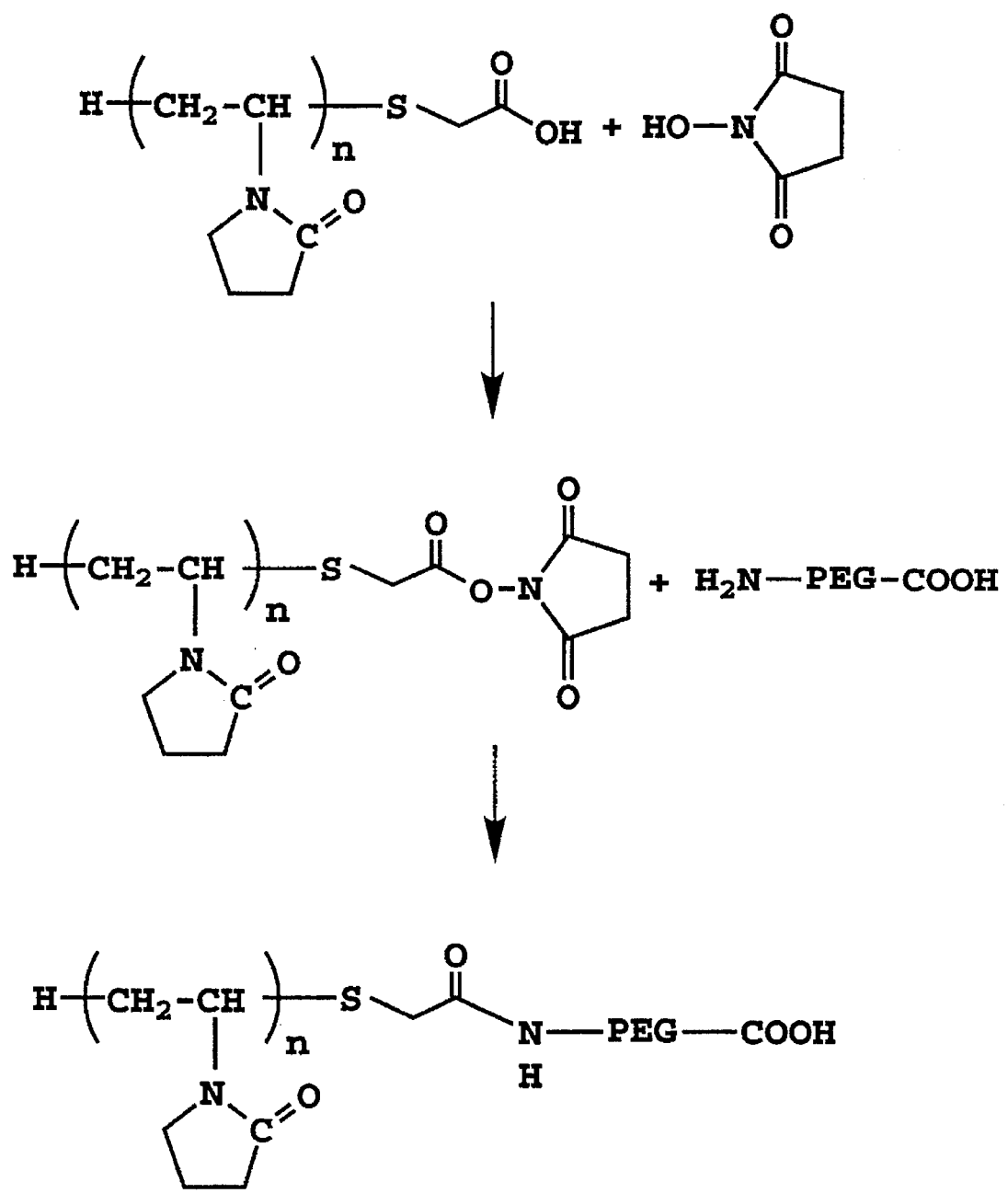
FIG. 5 illustrates a synthetic reaction scheme for preparing a block copolymer with polyvinylpyrrolidone and polyethyleneglycol segments.

FIG. 5 illustrates the synthesis of a block copolymer containing a PVP and a PEG block. A short PVP polymer chain prepared as described above can be coupled to a bifunctionalized PEG polymer chain containing terminal amine and carboxylic groups by standard coupling methods to generate an amide linkage (Zalipsky, 1986).

Other block copolymers containing blocks of PEG and blocks of any of the other homopolymers disclosed possessing the requisite solubility properties can be formed in a similar manner by reacting a homopolymer containing a chemical group at one of its ends with a bifunctionalized polymer chain.

Heteropolymers containing more than one alternating block of PEG and any of the disclosed homopolymers can be formed by reacting bifunctionalized PEG chains with bifunctionalized homopolymer chains in the presence of a linking reagent, such as a diisocyanate. The heteropolymer product should possess the requisite solubility properties. In a preferred embodiment the heteropolymer contains several alternating blocks of PVP and PEG.

C. Coupling Methods

In general the covalent attachment of polymers to a vesicle-forming lipid is accomplished by activation of chemical groups at one polymer end prior to reaction with a vesicle-forming lipid. A terminal hydroxyl, amine or carboxyl group may be activated for coupling to the lipid by monofunctional activating agents, such as N-hydroxysuccinimide, ethylchloroformate, DCCD, Woodward's Reagent K, cyanuric acid and trifluoromethanesulfonyl chloride among others. A number of bifunctional crosslinking reagents containing groups with different reactivities, such as some diisocyanates, may also be used to activate polymers prior to coupling to lipid components.

Figure 6:
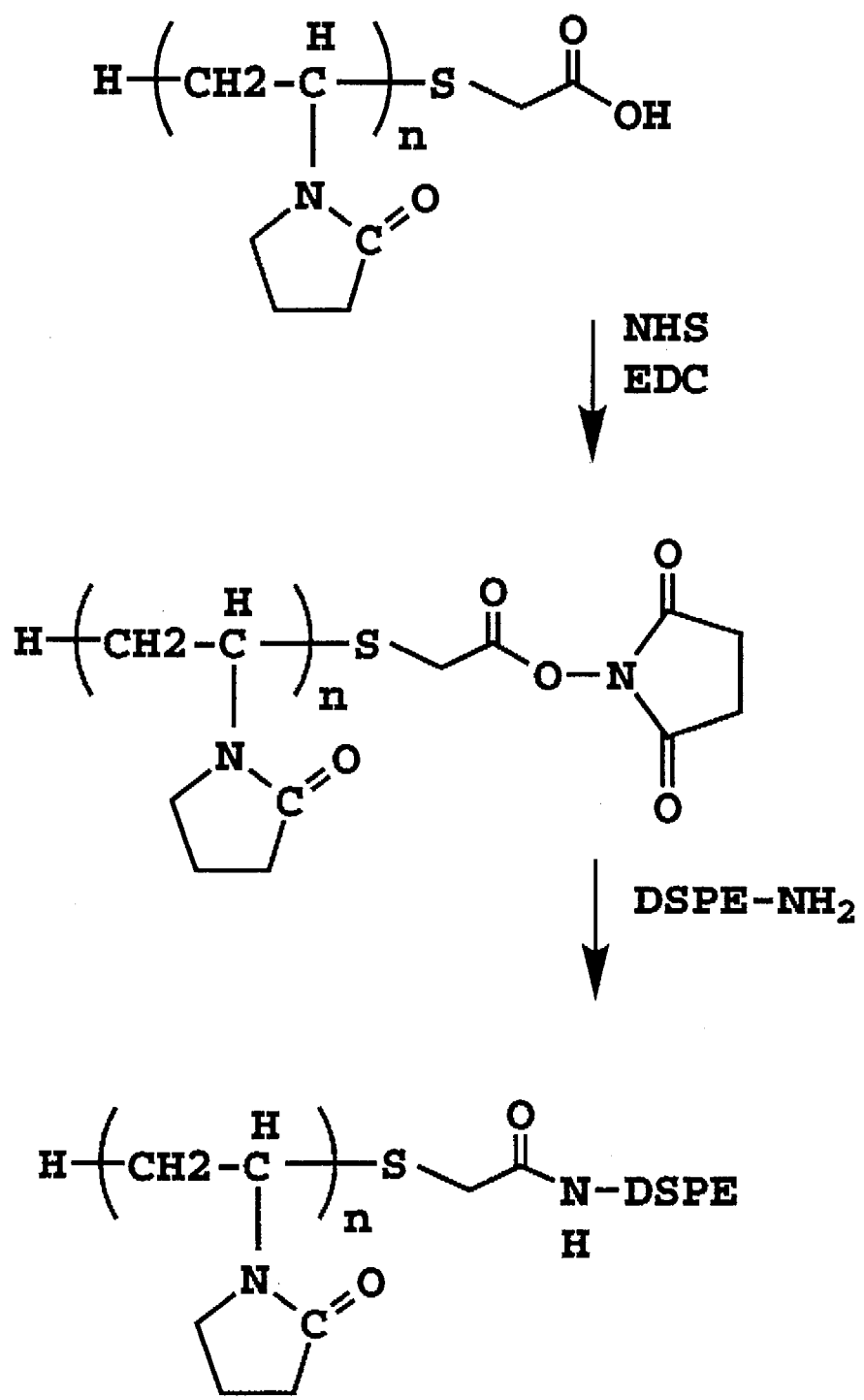
FIG. 6 illustrates coupling of polyvinylpyrrolidone to a phospholipid by use of N-hydroxysuccinimide.

A preferred method for activating a PVP polymer for attachment to a phospholipid is illustrated in FIG. 6. In this reaction the terminal carboxyl group of the polymer is activated by reaction with N-hydroxysuccinimide. After this activation step the polymer is reacted with an amino group-containing phospholipid, such phosphatidylethanolamine, to generate the polymer derivatized vesicle-forming lipid which is part of the composition of the invention.

Methods known to one skilled in art are available for activation of terminal hydroxyl groups (Zalipsky, 1992). In one such method, illustrated in FIG. 7, polymethyloxazoline is reacted with succinic anhydride to generate a carboxyl group at a polymer end. The terminal carboxyl group of the polymer is activated by reaction with N-hydroxysuccinimide. After this activation step the polymer is reacted with an amino group-containing phospholipid, such as phosphatidylethanolamine, forming the desired product.

Most of the polymers described in this invention can be coupled by either of the above described coupling methods. For coupling of derivatized celluloses, the polymers are incubated in the presence of an amine group-containing lipid without any prior activation step. Coupling can occur at the reducing end of the polysaccharide chain by reductive amination.

III. Liposome Composition

The polymer-lipid conjugate of the invention is used in preparing liposome compositions designed for use in delivering a drug via the bloodstream. In one embodiment the polymer-lipid conjugate, when incorporated at a mole ratio of preferably 1–30 mole percent in the outer lipid layer of the liposomes, forms a polymer layer which is effective to extend the blood circulation time of the liposomes severalfold over that of the liposomes lacking the polymer-lipid conjugate.

A. Lipid Components

The liposome is composed of underivatized vesicle-forming lipids and polymer-lipid conjugates which have been described above. The underivatized vesicle-forming lipids will form the bulk of the vesicle structure in the liposome.

Generally, these vesicle-forming lipids include any amphipathic lipids having hydrophobic and polar head group moieties, and which (a) can form spontaneously into bilayer vesicles in water, as exemplified by phospholipids, or (b) are stably incorporated into lipid bilayers, with its hydrophobic moiety in contact with the interior, hydrophobic region of the bilayer membrane, and its polar head group moiety oriented toward the exterior, polar surface of the membrane.

The vesicle-forming lipids of this type are preferably ones having two hydrocarbon chains, typically acyl chains, and a polar head group. Included in this class are the phospholipids, such as phosphatidylcholine (PC), PE, phosphatidic acid (PA), phosphatidylinositol (PI), and sphingomyelin (SM), where the two hydrocarbon chains are typically between about 14–22 carbon atoms in length, and have varying degrees of unsaturation.

The above-described lipids and phospholipids whose acyl chains have a variety of degrees of saturation can be obtained commercially, or prepared according to published methods. Other lipids that can be included in the invention are glycolipids and sterols, such as cholesterol.

The second type of lipid in the liposome composition is the polymer-lipid conjugate described in Section IIA. This polymer-lipid conjugate is included at a molar concentration sufficient to extend the blood circulation time of the liposomes severalfold over that of the liposomes lacking the polymer-lipid conjugate. The lipid conjugate is typically included at 3–10 mole percent, preferably about 5 mole percent.

One preferred embodiment of the polymer-lipid conjugate is a PVP polymer-derivatized distearylphosphatidylethanolamine (PVP-DSPE). The PVP chain is preferably a PVP chain having a molecular weight between 2,000–17,000 daltons, more preferably between 4,500 and 11,000 daltons. The lipid is preferably a PE, such as DSPE.

Another preferred embodiment of the polymer-lipid conjugate is a polymethyloxazoline-derivatized distearylphosphatidylethanolamine (PMOZ-DSPE). The polymethyloxazoline chain is preferably a chain having a molecular weight between 2,000–16,000 daltons, more preferably between 4,000 and 11,000 daltons.

B. Liposome Preparation

The liposomes may be prepared by a variety of techniques, such as those detailed in Szoka et al, 1980. One method for preparing drug-containing liposomes is the reverse phase evaporation method described by Szoka et al and in U.S. Pat. No. 4,235,871. In this method, an organic solution of liposome-forming lipids is mixed with a smaller volume of an aqueous medium, and the mixture is dispersed to form a water-in-oil emulsion, preferably using pyrogen-free components. The drug or other pharmaceutical agent to be delivered is added either to the lipid solution, in the case of a lipophilic drug, or to the aqueous medium, in the case of a water-soluble drug.

After removing the lipid solvent by evaporation, the resulting gel is converted to liposomes, with an encapsulation efficiency, for a water-soluble drug, of up to 50%. The reverse phase evaporation vesicles (REVs) have typical average sizes between about 0.2–0.4 microns and are predominantly oligolamellar, that is, contain one or a few lipid bilayer shells. The REVs may be readily sized, as discussed below, by extrusion to give oligolamellar vesicles having a maximum selected size preferably between about 0.05 to 0.2 microns.

To form MLV's, a mixture of liposome-forming lipids of the type detailed above dissolved in a suitable solvent is evaporated in a vessel to form a thin film, which is then covered by an aqueous medium. The lipid film hydrates to form MLVs, typically with sizes between about 0.1 to 10 microns. Typically, MLVs are sized down to a desired size range of 0.5 or less, and preferably between about 0.05 and 0.2 microns by extrusion.

One effective sizing method for REVs and MLVs involves extruding an aqueous suspension of the liposomes through a polycarbonate membrane having a selected uniform pore size, typically 0.05, 0.08, 0.1, 0.2, or 0.4 microns (Szoka). The pore size of the membrane corresponds roughly to the largest sizes of liposomes produced by extrusion through that membrane, particularly where the preparation is extruded two or more times through the same membrane.

Alternatively, the REV or MLV preparations can be treated to produce small unilamellar vesicles (SUVs) which are characterized by sizes in the 0.04–0.08 micron range. SUVs may be useful, for example, in targeting a tumor tissue which permits selective passage of small particles, typically less than about 0.1 micron, through the capillary walls supplying the tumor. As noted above, SUVs may be formed readily from fluid vesicle-forming lipids.

After final sizing, the liposomes can be treated, if necessary, to remove free (non-entrapped) drug. Conventional separation techniques, such as centrifugation, diafiltration, and molecular-sieve chromatography are suitable. The composition can be sterilized by filtration through a conventional 0.45 micron depth filter.

Although the polymer-lipid conjugate of the invention is preferably included in the lipid components used in forming liposomes, the conjugates may alternatively be incorporated into the outer liposome layer by diffusion into preformed liposomes. Typically, this is done by incubating preformed liposomes in the presence of the conjugate (which can exist in solution in micellar form) until a desired concentration of the conjugate has been taken up in the liposomes. The suspension may additionally contain surfactants, such as deoxycholate, to facilitate diffusion of the conjugate into liposomes. The surfactant can be removed subsequently, e.g., by dialysis.

The liposomes may be prepared to include surface-bound ligand molecules, such as antibodies, which are effective to bind specifically and with high affinity to ligand-binding molecules, such as antigens, which are localized specifically on target cells. As an example, the ligand molecules may be tumor-specific antibodies, for binding to tumor-specific antigens on tumor cells.

A variety of methods for coupling ligands to the surface of liposomes are known. One method includes incorporation of preformed ligand-derivatized lipid components into liposomes. Alternatively, ligands may be coupled to activated ends of polymer chains in a preformed liposome.

C. Surface Shielding Properties

The derivatized lipid-polymer conjugates prepared as above can be further selected for their ability to shield surface charge on liposomes. The shielding of surface charge can be measured, for example, by changes in the electrophoretic mobility of negatively charged liposomes, according to methods described below.

Table 2 shows the surface charge, zeta potential and the distribution ratio between the mononuclear phagocytic system (MPS) and blood for liposomes containing 3 mole percent of the lipid components at the left in the table. Here PC refers to phosphatidylcholine, PS refers to phosphatidylserine, PG refers to phosphatidylglycerol, $G_{T_1}$, $G_{D_{1a}}$, and $G_{M_1}$ refer to different gangliosides, and PEG-DSPE refers to distearylphosphatidyl-ethanolamine derivatized by PEG.

TABLE 2

| Lipid | MPS/Blood level (24 hr) | Surface Potential (mV) | |
|---|---|---|---|
| | | Surface Charge | Zeta |
| PC | 8.6 | 0 | 0 |
| PS | 188 | –6 | –8 |
| PG | 123 | –6 | –8 |
| $G_{T_1}$ | | –4.6 | –17 |
| $G_{D_{1a}}$ | | –6 | –12 |
| $G_{M_1}$ | 3.0 | –3.4 | –5 |
| PEG-DSPE | 0.7 | Equal to PG | –1.3 |

Ratios of liposomes in the mononuclear phagocytic system (MPS) and in the blood are used as a measure of the blood circulation lifetime of the liposomes in vivo, where a lower ratio indicates less uptake by the MPS and longer circulation in the bloodstream. The ratios shown in the table were determined for liposomes distribution 24 hours after intravenous administration, for example by the method described in U.S. Pat. No. 4,920,016. As seen, all of the formulations except the one containing PEG-DSPE gave MPS/blood ratios significantly above 1.

The surface charge values given in the table were calculated by standard methods, such as those described in McDaniel et al., and reflect the surface density of negative charges on the liposomes. It is noted that the surface charge has been determined with respect to selected ionic strength and pH of the liposome in addition to the mole content of the charged lipid components.

The zeta potential values in the table provide a measure of the apparent charge on the outer surface of the liposomes. These values are determined from the electrophoretic mobility of the liposomes, according to known methods (Woodle). The zeta potential values thus reflect the charge on the liposomes seen by the electric field during electrophoresis. A less negative zeta potential means that the liposomes have a lower apparent surface charge, as determined from a reduced migration rate in an electric field.

If the zeta potential values are lower than the surface charge values for any liposome formulation, the reduced zeta potential is likely indicative of screening of the surface charge. There is no charge shielding effect observed in liposomes containing PS, PG, $G_{T1}$, or $G_{D1a}$. The liposome formulation containing PEG-DSPE, however, shows charge shielding. The zeta potential of −1.3 mV for PEG-DSPE liposomes (Woodle) represents a severalfold drop in negative charge over liposomes containing phosphatidylglycerol (PG) (zeta potential of −8 mV). Liposomes containing either PG or DSPE have the same surface charge density as do PEG-DSPE liposomes, but the charge is not shielded. This charge shielding effect correlates with the low MPS/blood ratio observed for this formulation.

Liposomes containing $G_{M1}$ also exhibit charge shielding, but not to the same extent as do PEG-DSPE liposomes. $G_{M1}$ contains a negatively charged sialic acid group that extends away from the liposome surface into the aqueous phase. If the sialic group were located on the liposome surface, the surface charge would be expected to be comparable to that of PG or PEG-DSPE liposomes (−6 mV). However, the surface charge value is lower as expected from the location of the negative charge (−3.4 mV).

The zeta potential of $G_{M1}$, therefore, is reduced (−5 mV) when compared with a value of( −6 mV) which is the true liposome charge. Also, the zeta potential is lower than for PG liposomes even though the negative charges are closer to the zeta potential determining plane (Mclaughlin, McDaniel). The MPS/blood ratio for $G_{M1}$ liposomes is reduced compared to that of PG or PS liposomes, but is not as low as for PEG-DSPE liposomes.

More generally, in accordance with one aspect of the invention, the lipid-polymer conjugate employed in the liposome composition of the invention is preferably one that is effective to shield liposome charge to an extent effective to reduce the electrophoretic mobility of the liposomes with respect to the same liposomes in which a lipid with , such as phosphatidylglycerol, is substituted for the added conjugate. The lipid-polymer conjugate and phosphatidylglycerol both contain a single negative charge at its lipid polar head group and contribute to the surface charge on the liposomes.

IV. Utility

As noted above, the polymer layer formed on liposomes or on other colloidal drug delivery systems by the lipid-polymer conjugate functions to extend the blood circulation time of the liposomes severalfold. The enhanced blood circulation time, in turn, will allow a variety of therapeutic uses which are not effective in conventional, rapidly cleared liposomes. Some of these new therapeutic uses include:

1. Prolonged delivery of a drug by release from the particles, as they circulate in the bloodstream over an extended time.

2. Treatment of solid tumors. The long circulation time allows the particles to reach a tumor targeting site via the bloodstream, and to extravasate into the tumor region.

3. Treatment of infection or inflammation. As above, the long circulation time allows the particles to reach a site of infection or inflammation, via the bloodstream, and to extravasate into the region of infection.

A critical feature of the polymer layer on the liposome, as indicated above, is that the polymers forming the layer are soluble in an aqueous medium, but also soluble in one or more of a variety of polar organic solvents. Polymer solubility in water permits the polymer chains to extend away from the liposome surface out into the aqueous shell surrounding the liposome, and to effectively "fill" the aqueous shell. Polymer solubility in a variety of organic solvents and water suggests that the polymer chains are conformationally flexible, and thus are able to create a uniform local concentration of polymer chains around the outer surface of the liposomes forming an effective barrier to interactions between the liposome surfaces and blood components involved in liposome uptake from the blood.

The following examples illustrate methods of preparing lipid-polymer conjugates which can be incorporated in liposome compositions to enhance liposome circulation times in the bloodstream. The examples are intended to illustrate specific lipid-polymer conjugate preparations, but are in no way intended to limit the scope thereof.

EXAMPLE 1

Preparation of PVP-DSPE Conjugate

The polymerization of PVP, and attachment of PVP to DSPE described in this example is illustrated in FIGS. 1 an 6, respectively.

A. PVP Polymerization

A mixture of 25 g (0.23 mole) of N-vinyl-2-pyrrolidone, with 0.7 ml (10 mmole) mercaptoacetic acid (in a 70% aqueous solution) and 125 mg (0.76 mmole) of AIBN is diluted to 50 ml with methanol and kept at 60° C. with stirring under a nitrogen atmosphere. After 24 hours, 100 ml methylene chloride is added. The solution is dried over anhydrous sodium sulfate, filtered and poured with stirring into an excess of dry ether. The polymer is purified by dissolving in methylene chloride and reprecipitating into an excess of dry ether.

Product is further purified by size fractionation using a Bio Gel P60 column (5×50 cm) and water as the mobile phase. PVP polymers with a molecular weight of approximately 6,000 daltons (about 53 monomer units) are isolated.

B. PVP Attachment to DSPE

To activate the carboxylic acid of PVP for coupling to the amine group of DSPE the following protocol is utilized. To a solution of PVP6000, 10 g, 1.7 mmole in 50 ml of N,N-dimethylformamide (DMF) cooled to 10° C., and 0,575 g, 5 mmole of N-hydroxysuccinimide in DMF, and dicyclohexyl carbodiimide (1.032 g, 4.6 mmole) in DMF, are added. The solution is stirred overnight and the temperature is allowed to increase to room temperature. After removal of the precipitated dicyclohexylurea by filtration, the solution is concentrated to dryness under high vacuum. The residue is taken up in 50 ml of methylene chloride and the solution added dropwise to stirred diethyl ether (500 ml). The white precipitate is recovered by filtration and reprecipitated twice from methylene chloride/diethyl ether.

For attachment of PVP6000 to the polar head group of DSPE, to a chloroform solution (10 ml) of N-hydroxysuccinimide-ester PVP (0.8 mmole) is added DSPE (0.52 g, 0.70 mmole) TEA (0.2 ml, 1.4 mmole) to the reaction mixture. The mixture is maintained in an oil bath heated to 40°–45° C. for 2 hours. The formation of product is confirmed by TLC on silica plates (chloroform/methanol/water/concentrated ammonium hydroxide, (21.5/70/8/0.5).

EXAMPLE 2

Preparation of Polymethyloxazoline-DSPE Conjugate

Figure 7:
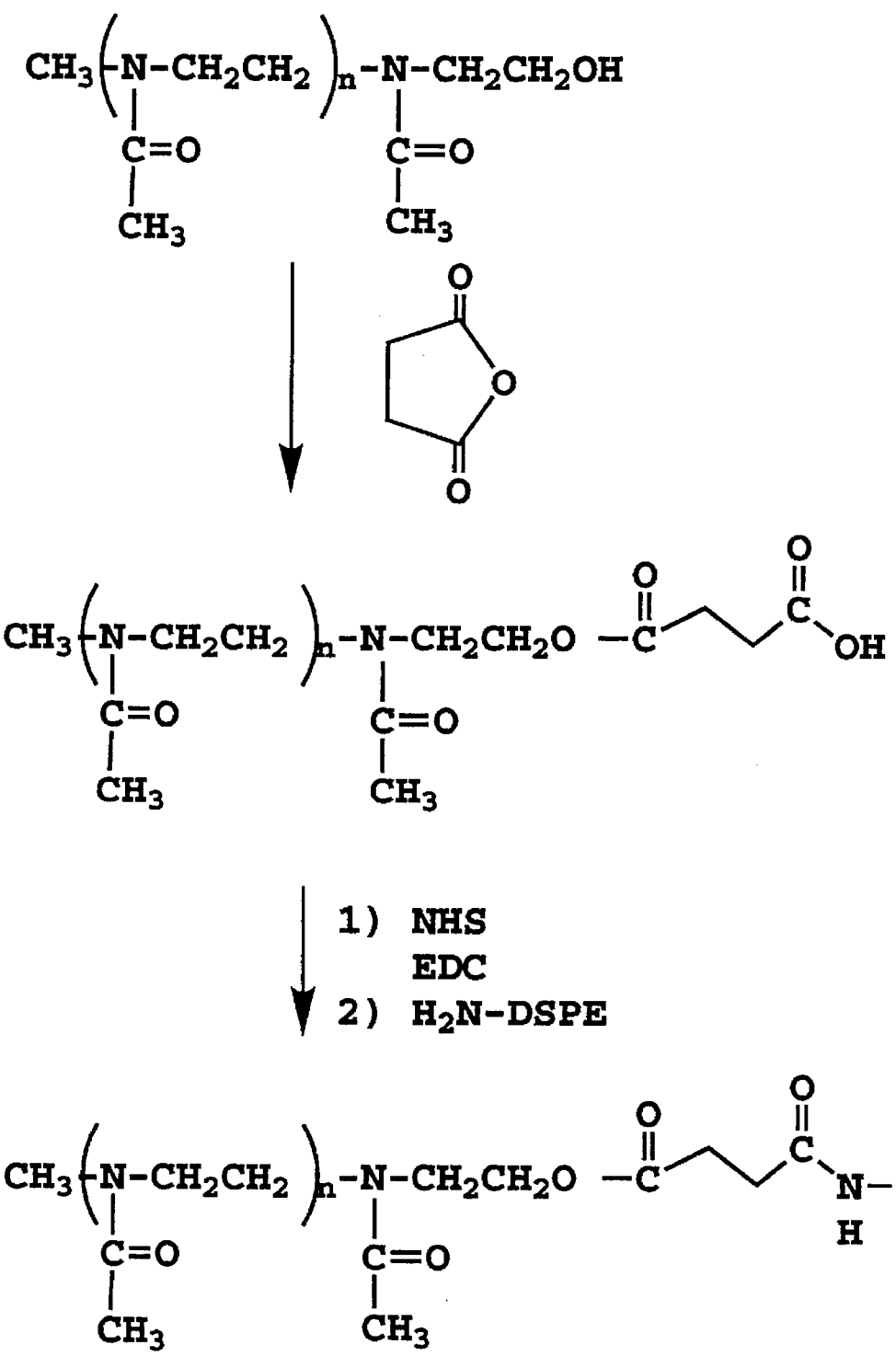
FIG. 7 illustrates conversion of the terminal hydroxyl group of polymethyloxazoline to a carboxylic acid group, and coupling of the polymer to a phospholipid through this carboxyl group.

The polymerization of 2-methyl-2-oxazoline, and attachment of the polymer to DSPE described in this example is illustrated in FIGS. 2 and 7, respectively.

A. Polymerization of 2-methyl-2-oxazoline

Cationic polymerization of 2-methyl-2-oxazoline (MOZ) is carried out by using methyltosylate (MET) as an initiator. To MOZ (3.2 mmole) ia added MET (0.07 mmole) in 1 ml acetonitrile. The reaction proceeds for 5 hours at 80° C. The polymerization product is precipitated two times with diethyl ether. The polymerization product is purified by sizing chromatography to isolate polymer species with about 30 to 60 monomer units. This corresponds to a molecular weight of about 2000 to 4000.

The product is dissolved in water to displace a tosylate group from one of the polymer ends.

B. Attachment of Polymethyloxazoline to DSPE

The terminal hydroxyl group can be converted to a carboxyl group by reaction with succinic anhydride prior to polymethyloxazoline attachment to DSPE. Polymethyloxazoline (10 mmole) and succinic anhydride (11 mmole) are mixed in 1,2-dichloroethane containing pyridine (10 mmole). The mixture is refluxed under nitrogen for four hours. After filtration and evaporation of the solvent, the residue is dissolved in methylene chloride and precipitated twice by addition of diethyl ether. The polymer attachment to DSPE is performed as described for PVP.

EXAMPLE 3

Polyaspartamide Synthesis

Aspartic acid (100 g) is polymerized by heating for 2 hours at 200° C. in an open tube. This polymerization reaction results in a polymer of 11,000 daltons. The polymer is dissolved in N,N-dimethylformamide and the solution is poured into a beaker containing 1 liter of water. A flaky precipitate is formed which is filtered, rinsed with water until neutrality, and dried in an oven at 110° C. for 24 hours.

Poly(D,L-succinimide) (30 g) is dissolved in dimethylformamide. Ethanolamine (45 ml) is added drop by drop and the solution is cooled in an ice bath to keep the temperature at 25°–30° C. The mixture is stirred for 2 hours and then neutralized with glacial acetic acid, diluted with water, dialyzed and lyophilized (Neri).

The single amino group of the polymer is used for the selective conjugation with lipid derivatives. For example, by reductive amination with periodate oxidized phosphatidylglycerol or phosphatidylinositol.

EXAMPLE 4

Preparation of VP/acrylamide-DSPE Conjugate

A. Polymerization of VP with Acrylamide Monomers

The VP/acrylamide copolymer is prepared in a similar fashion as described for the PVP homopolymer. N-vinylpyrrolidone (60 mmole) and acrylamide (67 mmole) with 0.7 ml (10 mmole) mercaptoacetic acid (in a 70% aqueous solution) and 125 mg (0.76 mmole) of AIBN is diluted to 50 ml with methanol and kept at 60° C. with stirring under a nitrogen atmosphere. After 24 hours, 100 ml methylene chloride is added. The solution is dried over anhydrous sodium sulfate, filtered and poured with stirring into an excess of dry ether. The polymer is purified by dissolving in methylene chloride and reprecipitating into an excess of dry ether.

Product is further purified by size fractionation using a Bio Gel P60 column (5×50 cm) and water as the mobile phase. PVP/AA copolymers with a molecular weight of approximately 6,000 daltons (about 53 monomer units) are isolated.

B. Attachment of PVP/AA Polymer Product to DSPE

The polymer is coupled to the vesicle-forming lipid by activating the polymer carboxyl group with N-hydroxysuccinimide prior to the addition of DSPE as described for Example 1.

EXAMPLE 5

Preparation of PEG/PVP Block Copolymer-DSPE Conjugate

A. Preparation of PEG/PVP Block Copolymer

A PVP chain containing a terminal carboxyl group is described in Example 1. Since the desired PVP product is to have an average molecular weight of about 3,000 instead of about 6,000 the concentration of MACA is increased from 0.2 M to 0.4 M. PEG chains with an average molecular weight of 2,000, each with one terminal amine and carboxyl group can be synthesized (Zalipsky). The two polymer segments are then coupled by first activating the PVP carboxyl group with N-hydroxysuccinimide ester and then reacting the activated carboxyl group with the amine group of PEG.

To activate the carboxylic acid of PVP for coupling to the amine group of PEG the following protocol is utilized. To a solution of PVP3000, 1 g in 10 ml of N,N-dimethylformamide (DMF) cooled to 10° C., and equimolar amounts of N-hydroxysuccinimide in DMF, and dicyclohexyl carbodiimide in DMF, are added dropwise. The solution is stirred overnight and the temperature is allowed to increase to room temperature. After removal of the precipitate dicylohexylurea by filtration, the solution is concentrate to dryness under high vacuum. The residue is taken up in 5 ml of methylene chloride and the solution added dropwise to stirred diethyl ether (100 ml). The white precipitate is recovered by filtration and reprecipitated twice from methylene chloride/diethyl ether.

For attachment of PVP3000 to PEG, to a methylene chloride solution of N-hydroxysuccinimide ester-terminated PVP (2.1 g, 0.70 mmole) is added the omegaamino acid derivative of PEG (1.4 g, 0.70 mmole) in 5 ml methylene chloride followed by TEA (0.2 ml, 1.4 mmole). The reaction mixture is stirred at 25° C. for 22 hours. The product is precipitated form the methylene chloride solution by addition of diethyl ether. This step is repeated several times.

B. PVP-PEG Block Copolymer Attachment to DSPE

To activate the carboxylic acid of PVP-PEG copolymer for coupling to the amine group of DSPE the following protocol is utilized. To a solution of PVP-PEG (MW=5000, 1 g, 0.2 mmole) in 4 ml of N,N-dimethylformamide (DMF) cooled to 10° C., and N-hydroxysuccinimide (30 mg, 0.26 mmole) in DMF (1 ml), and dicyclohexyl carbodiimide (59 mg, 0.26 mmole) in DMF (1 ml), are added. The solution is stirred overnight and the temperature is allowed to increase to room temperature. After removal of the precipitated dicylohexylurea by filtration, the solution is concentrated under high vacuum. The residue is taken up in 5 ml of methylene chloride and the solution added dropwise to stirred diethyl ether (100 ml). The white precipitate is recovered by filtration and reprecipitated twice from methylene chloride/diethyl ether.

For attachment of PVP-PEG (MW=5000) to the polar head group of DSPE, to the methylene chloride solution of N-hydroxysuccinimide ester terminated PVP-PEG copolymer (3.5 g, 0.70 mmole) is added is added DSPE (0.70 mmole) in 2 ml chloroform and TEA (0.2 ml, 1.4 mmole) are added to the reaction mixture. The mixture maintained on an oil bath heated to 70°–75° C. for 2 hours. The formation of product is confirmed by TLC on silica plates (chloroform/methanol/water/concentrated ammonium hydroxide, (21.5/70/8/0.5).

Although the invention has been described and illustrated with respect to particular derivatized lipid compositions, it will be apparent that a variety of modifications and changes may be made without departing from the invention.

It is claimed:

1. A liposomal composition containing liposomes having sizes between 0.05–0.5 microns, and comprised of vesicle-forming lipids and between 1–30 mole percent of a lipid-polymer conjugate consisting of a lipid polymer conjugate consisting of a lipid having two hydrocarbon chains as hydrophobic moieties and a polar head group, and covalently attached to said polar head group is a homopolymer or copolymer polymer chain having one end at which the polymer chain is attached to said polar head group and an opposite free end, said polymer chain containing a polymer selected from the group consisting of polyvinylpyrrolidone, polyvinylmethylether, polyhydroxypropyl methacrylate, polyhydroxyethyl metacrylate, polyhydroxyethyl acrylate, polymethacrylamide, polydimethylacrylamide. polymethyloxazoline, polyethyloxazoloine, polyhydroxyproploxazoline, and polyaspartamide.

2. The conjugate of claim 1, wherein the polymer chain is a homopolymer selected from the group consisting of polyvinylpyrrolidone, polyvinylmethylether, polyhydroxypropyl methacrylamide, polyhydroxypropyl methacrylate, polyhydroxyethyl acrylate, polymethacrylamide, polydimethylacrylamide, polymethyloxazoline, polyethyloxazoline, polyhydroxyethyloxazoline, polyhydroxypropyloxazoline, and polyaspartamide.

3. The conjugate of claim 1, wherein the polymer chain is a block or random copolymer containing one or more blocks of a first polymer spaced by blocks or single subunits of a second polymer, said polymers selected from the group consisting of polyvinylpyrrolidone,polyvinylmethylether, polyhydroxypropyl methacrylate, polyhydroxyethyl acrylate, polymethacrylamide,and polydimethylacrylamide.

4. The conjugate of claim 1, wherein the polymer chain is a block or random of copolymers containing one or more blocks of a first polymer spaced by blocks or single subunits of a second polymer, said polymers selected from the group consisting of polymethyloxazoline, polyethyloxazoline, polyhydroxyethyloxazoline, and polyhydroxypropyloxazoline.

5. The conjugate of claim 1, wherein the polymer chain is a block copolymer containing one or more blocks of polyethylene glycol spaced by blocks or single subunits of a second polymer selected from the group consisting of polyvinylpyrrolidone, polyvinylmethylether, polymethacrylamide, polydimethylacrylamide, polymethyloxazoline, and polyethyloxazoline.

6. The conjugate of claim 1, wherein the polymer is a homopolymer of polyvinylpyrrolidone.

7. The conjugate of claim 1, wherein the polymer is a homopolymer selected from the group consisting of polymethyloxazoline and polyethyloxazoline.

8. The conjugate of claim 1, wherein the polymer chain has degree of polymerization between about 20 to 150.

9. The conjugate of claim 1, wherein the vesicle-forming lipid is a phospholipid.

10. The conjugate of claim 9, wherein the vesicle-forming lipid is phosphatidylethanolamine.

11. A method of preparing liposomes characterized by an extended blood circulation time, comprising adding to vesicle-forming lipids, between 1–30 mole percent of a lipid-polymer conjugate consisting of a lipid polymer conjugate consisting of a lipid having two hydrocarbon chains as hydrophobic moieties and a polar head group, and covalently attached to said polar head group, is a homopolymer or copolymer chain having one end at which the polymer chain is attached to said polar head group and an opposite free end, said polymer chain containing a polymer selected from the group consisting of polyvinylpyrrolidone, polyvinylmethylether, polyhydroxypropyl methacrylamide, polyhydroxypropyl methacrylamide, polyhydroxyethyl acrylate, polymethacrylamide, polydimethylacrylamide, polymethyloxazoline, polymethyloxazoline, polyethyloxazoline, polyhydroxypropyloxazoline, and polyaspartamide, forming liposomes containing said vesicle-forming lipids and said lipid-polymer conjugate, and containing a pharmaceutical compound in entrapped form, and sizing the liposomes to a selected size in the size range between about 0.05 to 0.5 microns, where the added conjugate is effective to extend the circulation time of the liposomes when compared to liposomes prepared in the absence of said conjugate.

12. The method of claim 11, wherein the added lipid-polymer conjugate is effective to reduce the electrophoretic mobility of the liposomes with respect to the same liposomes in which phosphatidylglycerol is substituted for said lipid polymer conjugate.

* * * * *